United States Patent [19]

Augenlicht

[11] Patent Number: 4,981,783

[45] Date of Patent: Jan. 1, 1991

[54] METHOD FOR DETECTING PATHOLOGICAL CONDITIONS

[75] Inventor: Leonard Augenlicht, Stamford, Conn.

[73] Assignee: Montefiore Medical Center, Bronx, N.Y.

[21] Appl. No.: 852,401

[22] Filed: Apr. 16, 1986

[51] Int. Cl.$^5$ .................... C12Q 1/68; C12P 19/34; G01N 35/02; C12N 15/03

[52] U.S. Cl. .......................... 435/6; 435/91; 435/803; 436/501; 436/813; 536/27; 935/3; 935/9; 935/19; 935/29; 935/78; 935/80

[58] Field of Search ............... 435/6, 91, 803; 436/501, 813; 536/27; 935/3, 9, 19, 29, 78, 80

[56] References Cited

U.S. PATENT DOCUMENTS 4,699,877 10/1987 Cline et al. .................. 435/6

Primary Examiner—Amelia Burgess Yarbrough
Assistant Examiner—Ardin H. Marschel
Attorney, Agent, or Firm—Anthony J. Casella; Gerald E. Hespos

[57] ABSTRACT

A method is disclosed for the analysis of gene expression in human biopsy that is useful in the diagnosis and prognosis of disease and evaluation of risk for disease. The method comprises the steps of compiling data regarding the level of expression of certain individual cloned gene sequences from patients having defined pathological conditions and from normal patients and thereafter identifying sequences that characterize the pathological condition.

The data regarding the expression of the individual cloned genes are stored in a defined pattern or array. Replicas of this array are hybridized to radioactive probes made using the RNA isolated from biopsy tissue. The extent of hybridization of the probe to each of the cloned sequences is proportional to the level of expression of the cloned sequence in the tissue from which the probe was made. This may be done by exposing the hybridized clones to x-ray film and scanning the x-ray films to quantify the cloned sequences. This is preferably done with a computer driven scanner. The digitized data may be processed using a computer program. The method may be used to determine the expression of cloned sequences in human colon biopsy samples of malignant of premalignant tissue as well as for monitoring the effects of chemotherapeutic agents.

An apparatus is also disclosed for use in carrying out an automated assay.

13 Claims, 8 Drawing Sheets

METHOD FOR DETECTING PATHOLOGICAL CONDITIONS

BACKGROUND OF THE INVENTION

The mammalian cell contains approximately 50,000 genes encoded in its DNA. The level of expression of each of these genes can vary over a wide range, so that the possible combinations of gene activity is extremely large. While it is clear that a particular pattern of gene activity characterizes a cell in terms of its phenotypic properties, the very large complexity of the genetic material expressed has made it very difficult to compare overall gene activity between cells or tissue types. Previous data has relied upon the difficult interpretation of hybridization kinetics of very complex probes which represent the total number of genes that are active, or transcribed, in the cells or tissues under study.

The development of cloning methodology has in one sense made the analysis of differential gene expression much more simple. Using what are now standard techniques, individual gene sequences can be isolated in bacteria or other hosts and genes can be selected which are expressed only in a particular tissue, such as the globin gene in erythrocytes or the ovalbumin gene in oviduct, or which are expressed at different levels in two cell types or tissues which are to be compared. These purified gene sequences can then be radioactively labeled by a variety of procedures and used as probes to assay the level at which they are expressed in any tissue. Such probes can be used to distinguish, for example, an undifferentiated erythroid cell from a differentiated one as determined by the synthesis of the messenger RNA for globin, which is characteristic for erythroid differentiation. Approaches such as this, however, do not address whether there are changes in expression of the other 50,000 genes in the genome. For example, in comparing the messenger RNA population of the kidney to that of the brain and liver, hybridization kinetics suggest that many thousands of genes are differentially expressed in these tissues in addition to the few highly abundant sequences which may be characteristic of each tissue (Hastie and Bishop, 1976).

These considerations arise in all experiments which seek to analyze gene expression that accompanies the transformation of cells or when specific genes are sought which can be used to distinguish between normal cells and cells associated with neoplasic properties, such as malignancy, drug resistance, sensitivity, or invasiveness. For example, several of the proto-onc genes that are homologous to retroviral transforming genes have been shown to be elevated in expression in some human tumors (Slamon et al, 1984). It is not known, however, how many other changes there are in gene expression between any of these tumors and the corresponding normal tissue. The importance of this is illustrated by the fact that infection of normal chick embryo fibroblasts by the Rous sarcoma virus, which transforms the cells by introduction of the oncogene src and its subsequent expression, is accompanied by the appearance of approximately 1,000 new RNA transcripts (Groudine and Weintraub, 1980). Hence, even in this relatively simple case of viral transformation, where the etiological agent (the src gene) has been identified and is well understood, very complex changes in gene expression accompany, and may be the cause of, various properties that are characteristic of the transformation.

Cloning of gene sequences has become routine in many laboratories. Most cloning procedures are based on the original concepts of Stanley Cohen and Herb Boyer (U.S. Pat. No. 4,237,224). The procedures generally involve generating DNA molecules with "sticky" ends: that is, digesting the DNA with a restriction enzyme which leave short single stranded regions that are complementary to any other DNA molecule cut with the same enzyme. Hence, the DNA fragments containing the same sticky ends will hybridize to each other. In this way, DNA sequences from a eukaryotic genome, such as human, can be inserted into vectors, such as plasmids and viral genomes, which can be used to introduce the sequence into a bacterial host. Various methods may be utilized in the selection of bacteria which contain a particular cloned DNA sequence of interest.

One general class of procedures involves immobilizing the DNA from the bacteria or virus on nitrocellulose membrane filters. This can be accomplished in various ways. Bacterial colonies can be grown directly on, or transfered to, the filters. The colonies are subsquently lysed and washed in various buffers and the DNA immobilized on the filter by baking at elevated temperature under vacuum. This method was originally developed by Grunstein and Hogness (1975). A similiar method for transfering and fixing DNA from viral plaques was developed by Benton and Davies (1977). Purified DNA can also be fixed to nitrocellulose. When the DNA has been "fixed" to the filter by baking, the filter can be hybridized to probes which consist of nucleic acid (RNA or DNA) that has been labeled with radioactivity. Following washing to remove non-specifically bound material, the filter is usually exposed to x-ray film in order to obtain an image of the site at which hybridization has occured. The extent of hybridization can be determined by the intensity of the signal on the x-ray film. In this way, the bacteria or virus harboring a cloned sequence of interest can be located amongst a large number of bacteria or viruses.

The most common use of such procedures is the identification of a particular cloned sequence among a large number, by comparison with a plurality of known cloned sequences. For this, the probe used to hybridize to the cloned sequences on the surface of the filters must be enriched or purified in order for the sequence to be located. Other procedures involve hybridizing duplicates of the filters to two probes which are complex but differ in some significant way. For example, one can hybridize cloned sequences to probes made from two different cell or tissue types, the probes representing the total genetic complexity of the two types. Colonies on the replicate filters which hybridize differentially to the two probes then represent gene sequences which are differentially expressed in the two cell types. The procedure has been used to identify sequences which are differentially expressed during development in Xenopus (Dworkin and David, 1980), Aspergillus (Zimmermann et al., 1980) Dictyostellium (Williams and Lloyd, 1979) and sea urchin (Laskey et al, 1980). It has also been used to identify galactose inducible sequences in yeast (St John and Davis, 1979) and genes differentially expressed in human lymphocytes and fibroblasts (Crampton et al, 1980), and in various mouse tumors and normal tissues (Augenlicht and Kobrin, 1982).

Screening of libraries of sequences with these procedures has become routine in many laboratories. Usually, large numbers of clones are spread out at random. The screen is done, and a particular clone of interest is located by lining up the plate on which the clones are grown, the filter, and the x-ray film by use of reference marks. Gergen et al (1979) first enunciated the idea that replicas of an arrayed library would be extremely useful. Since the position of each clone in the array is known and reproducible, every time replicas of this are screened with a probe, one accumulates data on each member of the library. Gergen et al (1979) published procedures for storing clones in plates having a defined pattern of wells (one clone to a well) and of replicating this ordered library for screening purposes. However, as with most other work of a similar nature, this work did not quantitate the level of hybridization of each member of the library each time it was screened. Instead, qualitative evaluations of level of hybridization of some of the clones were recorded. While quantitation of level of hybridization is routine, Laskey et al made the first approach to quantitation of hybridization of members of an arrayed library. Using procedures similar to those published by Gergen et al (1979), they arrayed clones isolated from sea urchin and hybridized replicas of this arrayed library to probes made from sea urchin tissues at various stages of development (Laskey et al, 1980). The filters upon which the clones had been hybridized were then cut into sections and the sections counted to determine the amount of radioactivity hybridized to each clone. When compared to a set of standards, this gave an estimate of number RNA molecules per cell of each cloned sequence at stages of development of the sea urchin tissues.

The phenotype of a cell depends on the complement of genes that are expressed and the relative levels of expression of those sequences. For example, whether a tissue is malignant or benign, the site to which it would likely metastasize, its resistance or sensitivity to particular drug regimens, and the likely source of an unidentifiable tumor could be determined by comparing the pattern of expression of large numbers of sequences of an unknown sample to known patterns obtained. These may be compared by the use of a manual or automated technique.

An example of such a method for analyzing the level of expression of each of large numbers of genes is to hybridize dot blots of each of the sequences, or fixed bacterial colonies or phage plaques, each containing a different cloned sequence (Grunstein and Hogness, 1975; Benton and Davis, 1977) to a radio-labeled probe. The resulting hybridized filters are then cut into sections so that the radioactivity hybridized to each cloned sequence can be determined separately by counting in a liquid scintillation counter. This is precisely the manner in which the experiments of Laskey et al. (1980) were done.

The data which is stored in a computer data base can be compared from samples of known pathology. This permits the analysis of expression of large numbers of sequences that are used to distinguish phenotypes rather than qualitative or quantitative changes in a single or small number of genes. It has several advantages over the approach that is limited to a single gene. These advantages include the potential of detecting more subtle distinctions between related phenotypes (e.g., malignant cell types) and providing a means for detecting those phenotypes which may be determined by complex patterns of gene expression. Based on the assumption that malignancy or premalignancy may not be determined by changes in a single gene in human disease, the invention is based on the examination of a profile of a large number of genes.

SUMMARY OF THE INVENTION

The invention comprises a method for the determination of the presence of a malignant or premalignant condition in human tissue or determination of risk for development of malignant or premalignant conditions in human tissue such as the human colon mucosa. The disclosed method comprises the steps of:

(a) isolating RNA from the tissue that is to be determined;

(b) preparing a probe using RNA from step (a);

(c) hybridizing to the probe of step (b) a plurality of cloned gene sequences to form a hybridized probe;

(d) exposing the hybridized probe to detecting means to quantify the extent of hybridization; and (e) comparing the extent of the hybridization obtained in step (d) with a known standard to determine the existence of malignant or premalignant tissue or the presence of risk for the development of malignant or premalignant conditions in human tissue.

It is an object of this invention to provide a method for detecting pathoglogical conditions by the determination of expression genes that characterize pathological conditions such as colon cancer.

It is also an object of this invention to provide a novel automated process and apparatus for processing the prepared samples in order to determine the cloned sequence.

DESCRIPTION OF THE PREFERRED EMBODIMENT

Figure 1:
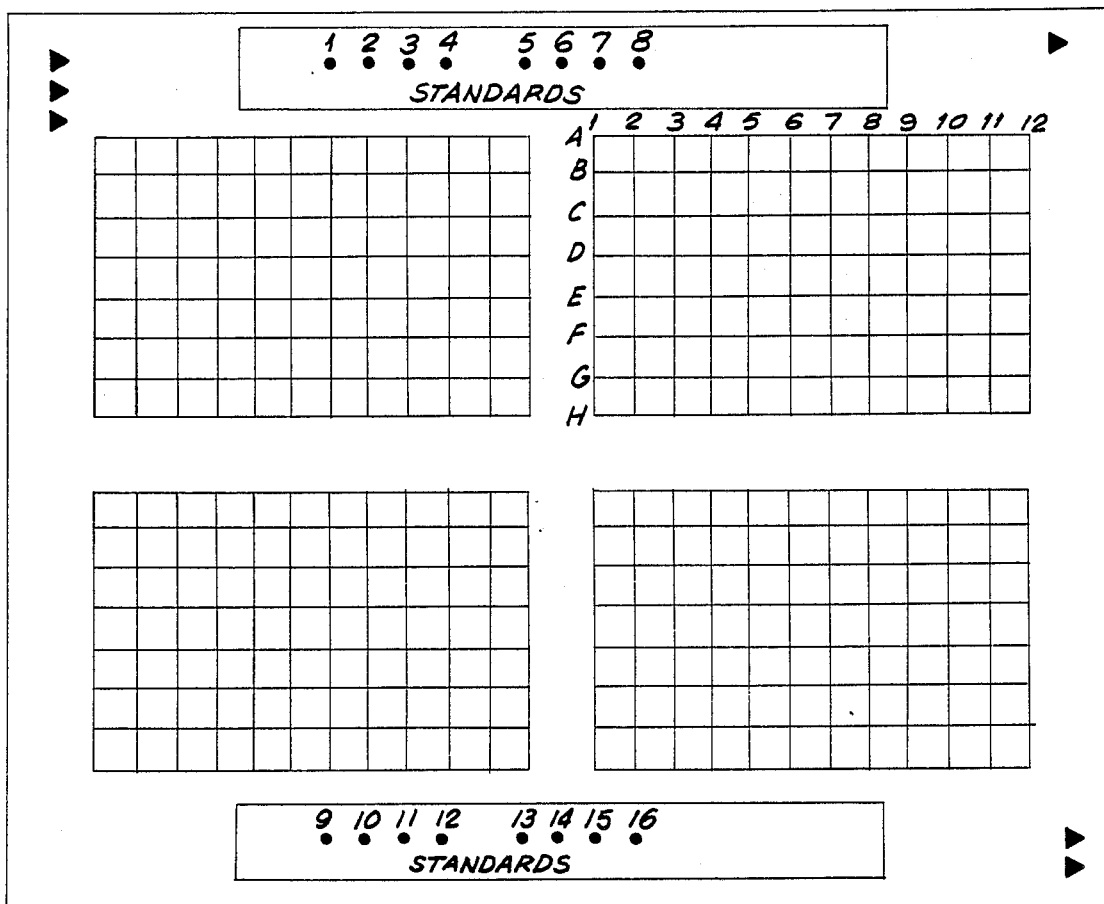
FIG. 1. is a reproduction of the standard format used in the evaluation of the library.

A plurality of cloned gene sequences otherwise referred to as the cloned gene libraries is prepared from genomic DNA fragments or the mRNA population. A poly A+ RNA of a human colon carcinoma cell line is used since this represents the subset of expressed genes in the carcinoma.

RNA is prepared from tumors grown in nude mice innoculated with HT-29 (available from American Type Culture Collection as ATCC HTB-38) cells by rapid disruption of the tumors in guanidinium isothiocyanate with a Polytron tissue disrupter followed by pelleting of the RNA through a CsCl cushion as described by Maniatis et al (1982). Poly A+ RNA is prepared from 1.8 mg of this RNA by chromatography on oligo dT cellulose by the method of Aviv and Leder (1972). 7 ug of polyA+ RNA is used to make cDNA by incubation with RNA dependent DNA polymerase (reverse transcriptase) isolated from avian myeloblastosis virus. Following the reaction, the RNA is hydrolyzed by incubation in 0.33N NaOH at 37 C. overnight. The NaOH is neutralized by addition of 5N acetic acid, the material extracted with phenol and the aqueous phase reextracted with ether. The cDNA is then precipitated with ethanol and the pellet rinsed in 100% ethanol and dried. The second strand of DNA is made by incubating the cDNA with DNA polymerase I Klenow fragment isolated from E. coli. Following completion of second strand synthesis, the DNA is digested with S1 nuclease from Aspergillus to digest single stranded DNA and cleave the hairpin expected at the end of duplex. The resulting double stranded (ds) DNA is precipitated with ethanol. Analysis of the product by agarose gel electrophoresis shows that the bulk of the dsDNA is 300–900 nucleotide in length. 84 ng of product is recovered. The dsDNA is tailed with deoxycytidine by incubation with terminal deoxynucleotide transferase. Following the reaction, the material is adjusted to 0.1 mM EDTA, 0.15M NaCl and mixed with 500 ng Pst I digested, deoxyguanosine tailed PBR 322 and incubated overnight to insert the C-tailed dscDNA into the G-tailed plasmid PBR 322. The final volume of the reaction is 200 ul. 50 ul is used on each of four separate occasions for transfecton into E. coli strain LE-392 which are made competent for uptake of plasmid by incubation in CaCl$_2$ as described by Dagert and Ehrlich (1979). Following transfection, the bacteria are spread on 1% agarose plates containing 15 ug/ml tetracycline in order to select for bacteria which take up the plasmid containing the gene for tetracycline resistence. 4,069 clones are obtained in total, of which approximately 5% appear to be non-recombinants as determined by their ability to grow on ampicillin.

Using sterile toothpicks, 4,032 individual clones are picked and innoculated individually each into a well of 96 well microtiter plates. Each plate consists of 96 wells in a defined pattern of 8 (vertical) by 12 (horizontal). Such plates are available from several suppliers, e.g., Falcon Plate 3072 (BD & Co.). The arrayed library therefore consists of 42 such plates. The last two positions for each plate are innoculated with LE-392 and with LE-392 harboring plasmid PBR 322. These serve as controls for subsequent screening (see below). The medium in the wells has been described by Gergen et at (1979) and contains 15 ug/ml tetracycline to maintain selective pressure for retention of plasmid. The plates are incubated at 37 C. overnight to grow the clones. This permanent library is then stored at -80 C. in a Revco Ultralowfreezer. The medium used permits recovery of viable bacteria even following many cycles of freezing and thawing (Gergen et al., 1979).

A replicating device is made which consists of 96 stainless steel prongs embedded in an aluminum base in the same pattern (8×12) as the 96 wells of the microtiter plates. This can be sterilized by autoclaving or by dipping the prongs into ethanol and flaming the ethanol in a bunsen burner. To replicate the clones in the 8×12 pattern onto nitocellulose filters, each plate is allowed to defrost. The replicating device is then sterilized, inserted into the 96 wells, and then imprinted on a rectangle of nitrocellulose (BA 85, Schleicher and Schuell) which is placed on a piece of sterile Whatman number 1 filter paper on a hard surface. Three such filters can be imprinted before the replicating tool must be recharged by introduction back into the microtiter plate. This procedure is repeated for each of the microtiter plates. The clones are then grown by placing each filter onto a petrie dish containing 1% nutrient agar with 15 ug/ml tetracycline. The plates are incubated until the colonies grow to approximately two mm in diameter and the filter is then transferred to an agar plate containing 150 ug/ml chloramphenicol and incubated at 37° C. for a further 24 hours. This latter step amplifies the copy number of the plasmid in each bacteria, but it is not necessary if a sufficiently high specific activity probe is made or if a small number of filters is to be hybridized so that it is not necessary to dilute the probe. The colonies are lyzed by placing the filters on Whatman 3MM paper saturated with 0.5N NaOH and washed as previously described (Grunstein and Hogness (1975)). The DNA of each colony is then fixed to the nitrocellulose by baking the filter at 80° C. for 90 minutes under vacuum. The filters are sealed in plastic bags and stored at 4° C. until use.

Preparation of probes.

Biopsy samples of human colonic mucosa, colonic adenomas and carcinomas are taken using a flexible colonoscope and placed into liquid nitrogen within 1 minute of removal. The samples are stored in liquid N2 until used. RNA is prepared from the biopsy material by rapid disruption of the tissue in a buffer containing guanidinium isothiocyanate and pelleting the RNA through a cushion of CsCl as described by Maniatis et al (1982). PolyA+RNA is isolated by chromatography on oligo dT cellulose by the method of Aviv and Leder (1972). The PolyA+RNA is used to prepared 32 P labeled cDNA probes as described by Augenlicht and Kobrin (1982).

Hybridization to the library.

A replica of the library consists of 1 each of the 42 filters, each filter containing 94 colonies and a positive and negative control for growth and hybridization (LE 392 and LE 392 containing PBR 322). Each probe made from a biopsy sample is hybridized to a complete replica of the library as follows. Each of the filters are prehybridized by incubating them at 65 C overnight in 200 ml of a buffer containing 5X SSPE (SSPE=0.18M NaCl, 0.01M $H_2PO_4.H_2O$, pH 7.7, 0.001M ethylenediaminetetraacetic acid), 5X Denhardt's reagent (Denhardt's=an aqueous solution of 0.02% each of ficoll, polyvinylpyrollidonc, and bovine serum albumin, 0.5% sodium dodecyl sulfate (SDS) and 8.4 mg of sheared salmon testes DNA denatured by boiling for 10 minutes. The filters are then placed into 200 ml of the same buffer containing the 32P labeled cDNA probe that is denatured by boiling, and incubated at 65° C. for a further 36–48 hours. The filters are washed twice in 2X SSPE, 0.5% SDS for 15 minutes at room temperature and six times in 1X SSPE, 0.1% SDS at 65° C. Autoradiography.

The 42 filters of each library replica are arrayed on copies of the format shown in FIG. 1. Each format can accommodate 4 filters so the entire replica set of 42 filters is aligned on 11 copies of the format. Group A contains filter 1–4, group B filters 5–8, and so forth. The filters are arranged in each format consecutively beginning with the upper left quadrant (labeled 1 in the figure), upper right (11), lower left (111) and lower right (IV). Each group of four filters (groups=A-K) also contains two strips of standards, which are located on the top and bottom of the format, and are labeled "standards 1–8" on the top and "standards 9–16" on the bottom. Since the filters containing the hybridized clones and standards were always aligned on the format precisely as described, the relative positions of all clones and standards is fixed. Each format also contains fiducial markings which can be used to line up the format for scanning and analysis. These are the triangles shown in FIG. 1. After the filters and standards are aligned as described, the formats are placed in metal X-ray cassettes, overlaid with a sheet of Kodak XOMAT AR-5 double sided X-ray film, and a Dupont intensifying screen. Exposure is at (−)80° C. for a period of time equal to the product of the input cpm for each probe at the beginning of the exposure x minutes which equals $5.8 \times 10^{10}$. The films are then developed in a Kodak X-ray processor. Since there are 11 formats for each probe, this generates 11 films which encompass the results for hybridization of a replica of the library for each probe.

Scanning the films and data digitization.

Each film is scanned with an Eikonix scanner, model 785, supported by a VAX 11/780 computer (Digital Equipment Corporation). The data are subsequently analyzed and processed using an IP 8500 image processing system (Gould) supported by the VAX 11/780 and an AP 120B array processor (floating point system).

The Eikonix scanner records signal from the X-ray films in areas called pixels. The signal consists of the % transmitted light and is collected using a 45 mm wide angle lens. It is then converted to optical density for each pixel. The pixel size is set at 100×100 microns, and the film is therefore divided into a grid 2048×2048 pixels for a total of $4.19 \times 10^6$ individual measurements for each film (11 films=1 complete replica of the library hybridized to one probe). Each of these values represents an 8 bit optical density value obtained from a 12 bit transmission value.

The resultant image is first processed with a 5×5 median filter to suppress grain and other high frequency noise. This procedure replaces each pixel with the median value of the pixels in the 5×5 neighborhood surrounding it. Background is then subtracted in two steps. An intermediate image is produced from the median filtered image by choosing the minimum value of a 161 pixel horizontal line centered at the element being generated. The actual length of the line is not critical as long as it is wider than the region reserved for an individual clone. A second intermediate image is produced from the first in the same manner except that a maximum value is used in place of the minimum value. This image is then subtracted on a pixel by pixel basis to produce the processed image from which clone measurements are made.

Reduction of the data.

In order for the data to be recorded for each clone, the position of each on the format is defined within the computer program. To do this, a template is defined using the processing system and the VAX 11/780 by scanning a copy of the format (FIG. 1) as described, and entering the position of the fiducial marks, each standard, and the intersection of each of the lines in grids I, II, III, and IV, which are the positions of the clones. The position of the fiducials is marked on each film scanned. Hence, when the fiducial positions are entered for each scan, the position of each clone and standard is identified by reference to the template. When this is done, the program then defines an area of 0.5 cm in diameter centered on each position and records the maximum optical density (pixel) within that area. Maximum optical density rather then integrated area is used since the growth of the clones is variable and differences in areas could contribute to the error. This problem may be eliminated by improvements of the system using purified DNA rather then lyzed, fixed bacterial colonies on the filters. Following entry of the fiducial marks, the program records the optical density for each of the clones which is proportional to extent of hybridization of the probe. This is done for each of the 11 films of a replica of the library.

Each format (FIG. 1) scanned may contain a series of standards representing a range of fractions of the input probe used for the hybridization. This permits normalization of the results for different probes since a plot can be made which relates spot density to input. The data for each clone may then be recalculated using the corresponding plot to express the data as percent hybridization of the input probe.

Initial Screening.

Initially the four thousand member cDNA library from HT-29 cells in patterned arrays is evaluated by means of six separate probes from six different biopsies. Two probes are made from the RNA of biopsies of flat colonic mucosa from individuals at low risk for colon cancer (no colon cancer for at least 2 generations), two probes are made from biopsies of adenomatous polyps of subjects with the genetic syndrome ACR (adenomatosis of the colon and rectum), and the final two probes are from biopsies of two colon cancers in subjects at undefined risk.

Following evaluation with these six probes, the resulting data permit us to select a sub-set of clones of potential interest for further screening. First, from the 4032, the number is reduced to 490 by eliminating all those clones which are expressed at a low abundance (essentially at background level) in all six biopsy samples. Control experiments demonstrate that no more than 5% of the clones are non-recombinants as determined by ampicillin resistence, and it is expected that a large number of the initial clones screened would be of low abundance. No preselection for moderate or high abundance sequences is made since we do not want to eliminate the possibility of detecting a major change in expression from the low to high abundance class.

Another 111 clones are eliminated from the sub-set since these are all expressed at levels modestly above background and show no variation in expression in the six biopsies. The decision to eliminate these sequences is a practical one. Decreasing the number of clones to 379 (with additional positive and negative controls) permits the scanning of a single film, rather than 11 films for the entire library, and simplifies the screening.

Each of the 379 clones is physically picked from the original library and innoculated into a new position in one or four 96 well microtiter plates to assemble a sub-library of these clones. Position H-12 in each plate contains LE-392 harboring the plasmid PBR-322. This position serves as a hybridization background spot for each filer in subsequent analysis of hybridization. In addition, the first plate contains no bacteria in position H-11, and serves as a control for antibiotic selection during growth of each replica of the sub-library.

Further screening.

Replicas of this sub-library are hybridized against probes made from biopsies of tissue of the three groups described above, and a fourth group: biopsies of flat mucosa from individuals with ACR. These are individuals at very high genetic risk for development of colon cancer. The relative level of hybridization is quantitated as described above.

The data for the 379 clones for each probe (biopsy) is then normalized as follows: The value for position H-12 in each quadrant of the format (PBR 322 background spot) is subtracted from every other value in that quadrant. Each value is then expressed as its ratio to the average of the values for all 379 clones for the probe. For each probe, this normalizes the value for each clone to the total hybridization for all clones. Hence, this step corrects for differences in probe specific activity, minor variations in filter hybridization or washing (e.g., temperatures, salt concentration), and exposure.

Data analysis.

Figure 2A:
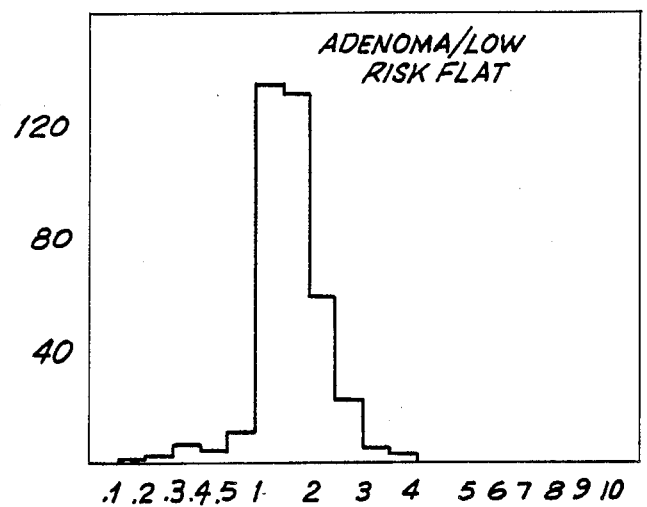
FIG. 2. is a comparison of tissues that is based on the use of the normalized hybridization values for each of the 379 clones in the sub-library, the mean hybridization of each clone was calculated for each of the four tissue groups: low-risk flat mucosa (n=6); high-risk flat mucosa (n=7); adenoma (n=6); carcinoma (n=7). For each clone, the six possible two-way comparisons of these 4 groups were then analyzed by calculating the ratio of mean hybridization (expression) for clone N in one group to the mean hybridization for clone N in the second group and the distribution of these ratios plotted as histograms. Ordinate, number of clones (of the 379); abscissa, ratio of expression in one tissue group as compared to another: (a) ratio for each clone in adenoma: low-risk flat mucosa; (b) carcinoma: low-risk flat mucosa; (c) carcinoma: adenoma; (d) high-risk flat mucosa: low-risk flat mucosa; (e) adenoma: high-risk flat mucosa; and (f) carcinoma: high-risk flat mucosa.
Figure 2B:
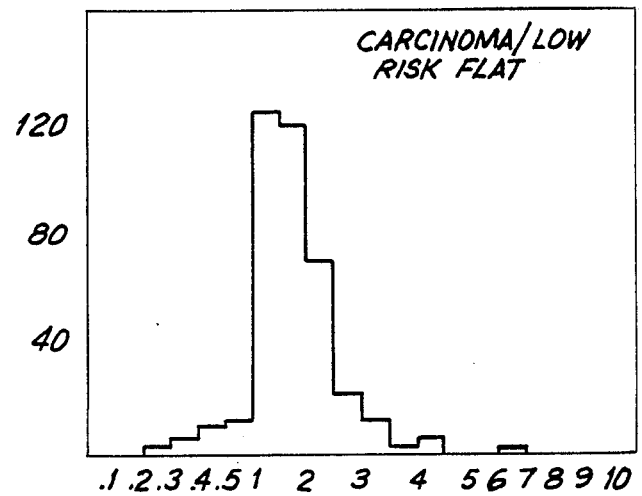
Figure 2C:
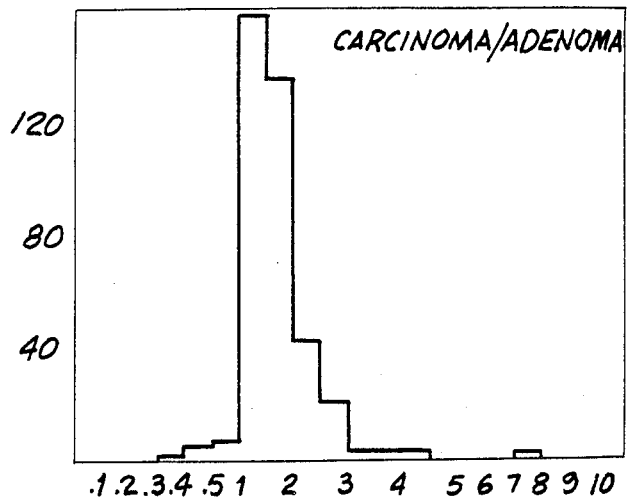

The mean and standard deviation of the normalized hybridization value for each sequence is calculated for each of the four tissue groups. In FIG. 2 the mean value for each clone is compared in the six possible two-way pairs of the four tissue groups. Each panel (a-f) shows one of the possible comparisons. The data is presented as the distribution of the number of sequences (out of the 379) which are at a particular ratio in one tissue group as compared to another. Thus, FIG. 2a illustrates a comparison of the average expression of each sequence in the adenomas to its average expression in the low risk flat mucosa biosies. Most sequences show little difference in expression, exhibiting ratios of expression in the two tissues of between 1 and 2. None of these minor differences are statistically significant. Some sequences do however show greater differences in expression. Eight sequences are increased in expression 3 to 4 fold in the adenomas compared to the low-risk flat mucosa (ratio on abscissa of FIG. 2a of 3 to 4) and nine are decreased in expression by 60 to 90% (ratio on abscissa of 0.1 to 0.4). A similar picture emerges from a comparison of each sequence in carcinomas to the low-risk flat mucosa (FIG. 2b) and each sequence in the adenomas to the carcinomas (FIG. 2c), although in each of these comparisons, a sequence is elevated in expression between 6 and 8 fold. The greatest number of differences is found in comparing the two extremes: carcinoma to low-risk flat mucosa (FIG. 2b). Here, 20 sequences are elevated greater than 3 fold and 11 sequences decreased more than 60%.

Figure 2D:
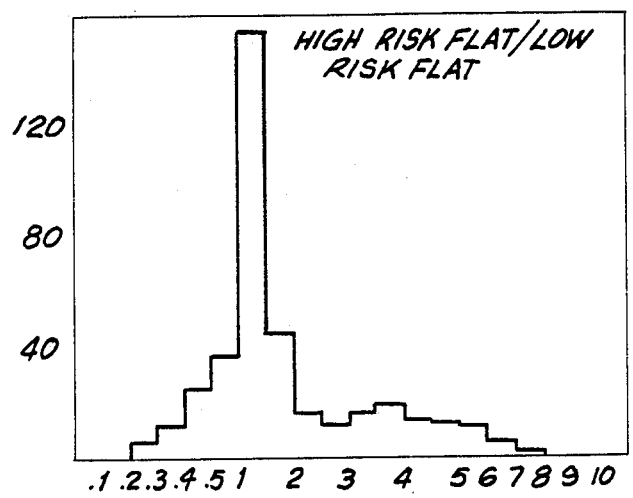
Figure 2E:
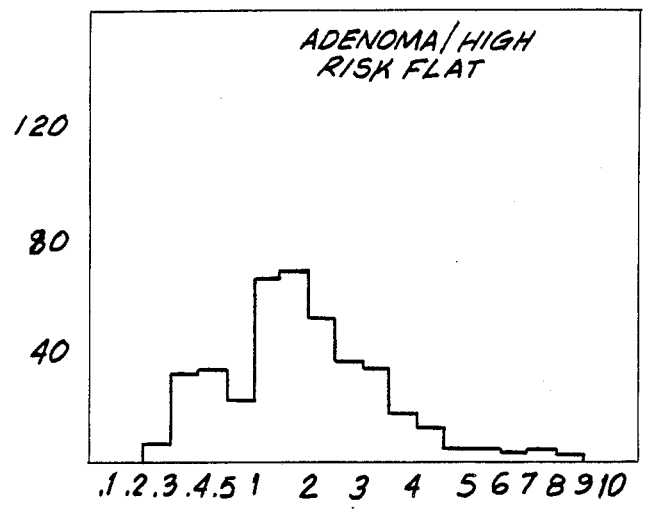
Figure 2F:
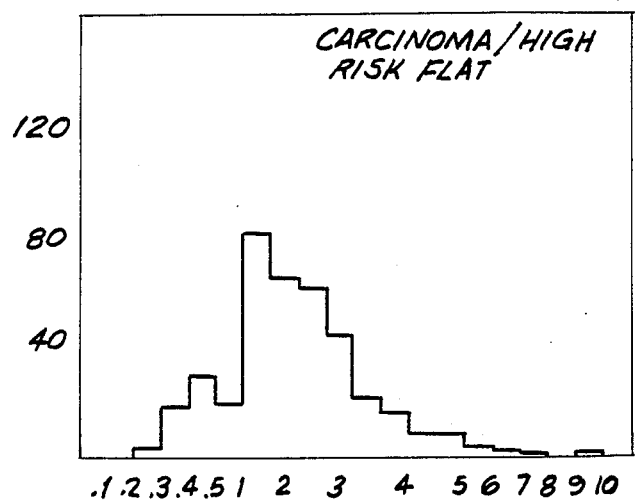
Figure 3:
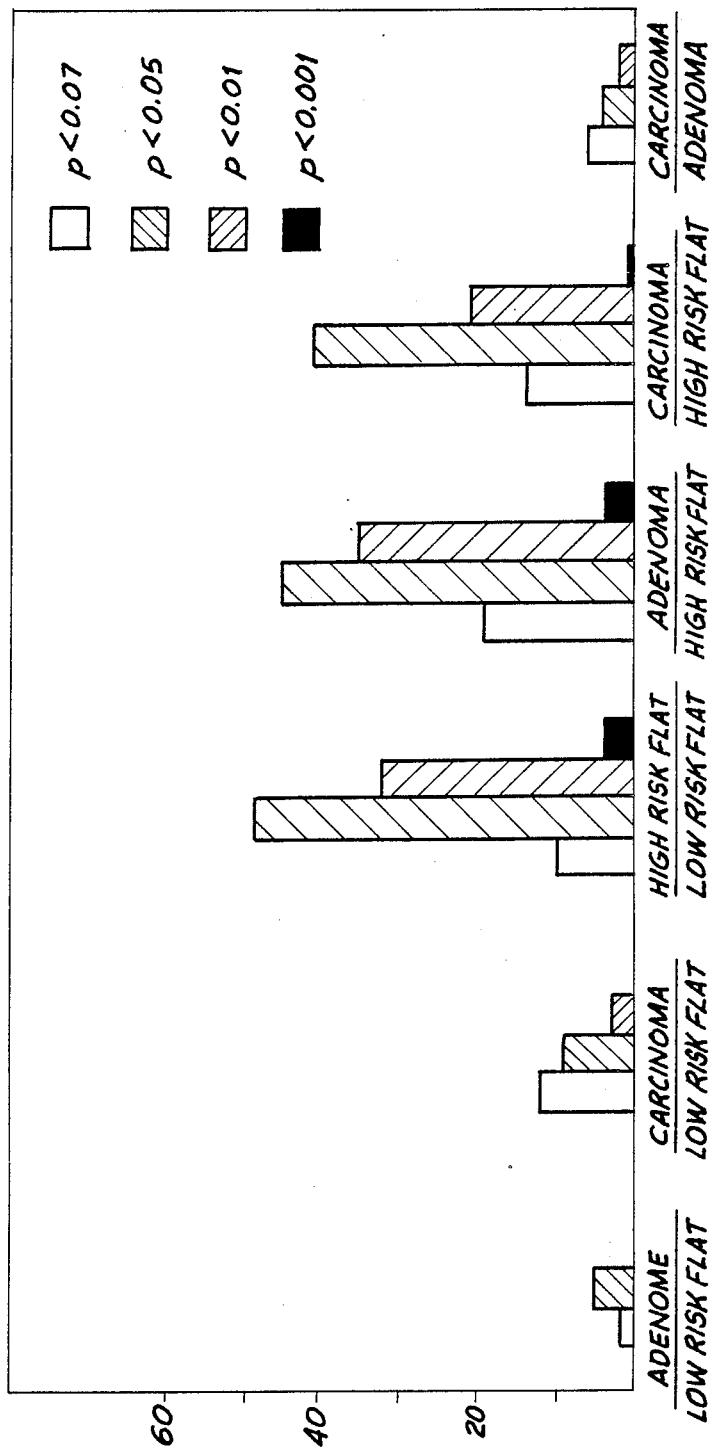
FIG. 3. shows the distribution of sequences which differ at various significance levels. The significance level (Student's t test) of the difference of expression of each clone in each comparison of the tissue groups (FIG. 2) was calculated and the distribution of these values plotted as a histogram for each comparison: □, $p<0.07$; ▨, $p<0.05$; ▧, $p<0.01$; and ■, $p<0.001$.
Figure 4A:
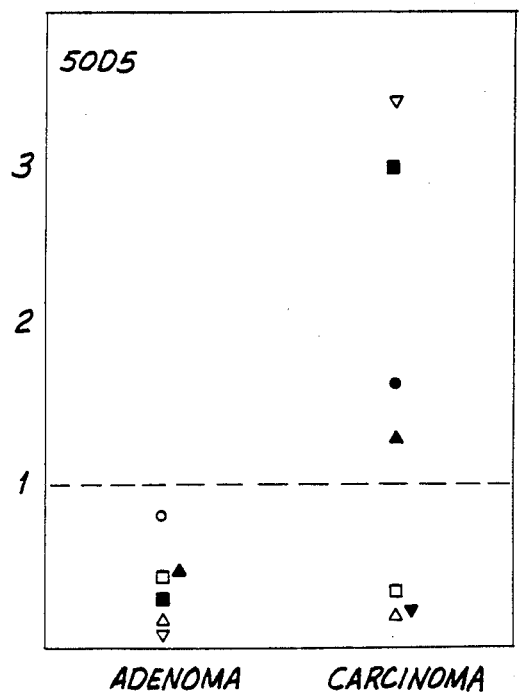
FIG. 4. shows the hybridization values for individual clones in adenoma and carcinoma biopsies. The normalized hybridization values (ordinate) for each of the adenoma and each of the carcinoma biopsies (abscissa) is plotted for clones: (a) 50D5; (b) 51A12; (c) 51E2; and (d) 52B10; adenomas: ●, #3; □, #10; ▽, #15; ■, #16; ▲, #19; carcinomas: ●, #1; □, #2; △, #11; ▽, #12; ■, #23; ▲, #26; and ◀, #28.
Figure 4C:
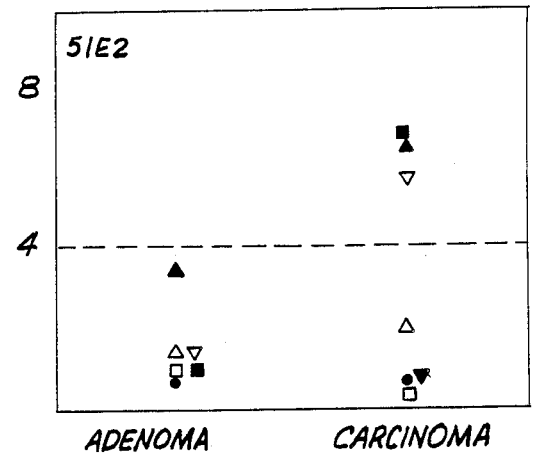
Figure 4B:
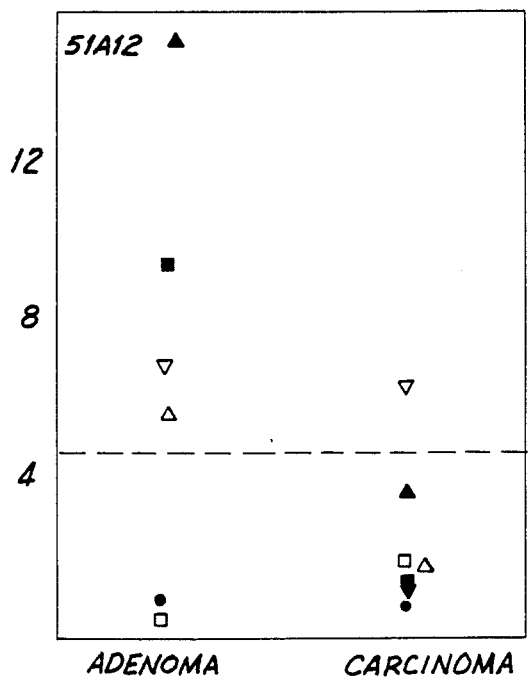
Figure 4D:
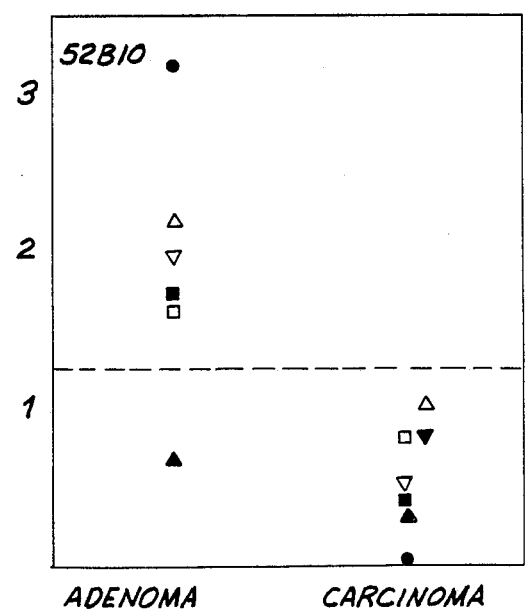
Figure 5A:
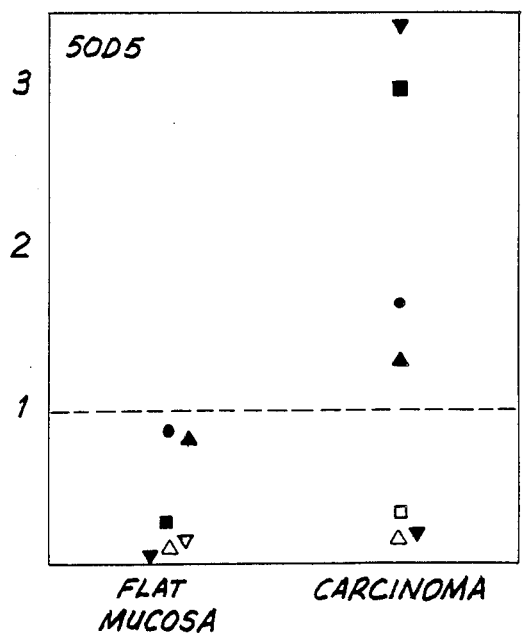
FIG. 5. shows the hybridization values for individual clones in low-risk flat mucosa biopsies and carcinoma biopsies. The normalized hybridization values (ordinate) for each of the low-risk flat mucosa and carcinoma biopsies (abscissa) is plotted for clones: (a) 50D5; (b) 51E9; (c) 52A12; (d) 52C9; and (e) 50A3; low-risk flat mucosa biopsies: ●, #5; △, #14; ▽, #17; ■, #20; ▲, #24; ◄, #27; carcinomas: ●, #1; □, #2; △, #11; ▽, #12; ■, #23; ▲, #26; and ◄, #28.
Figure 5C:
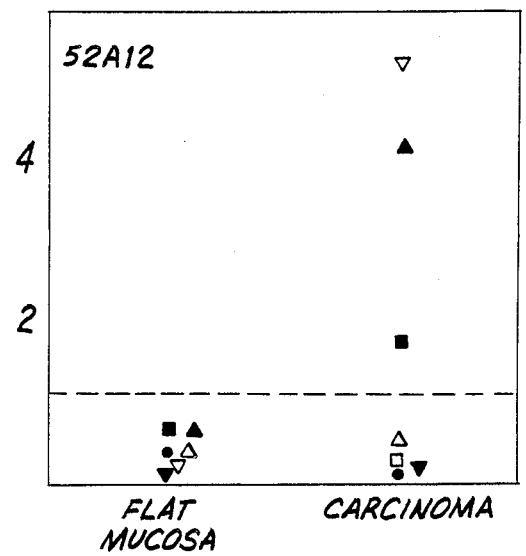
Figure 5B:
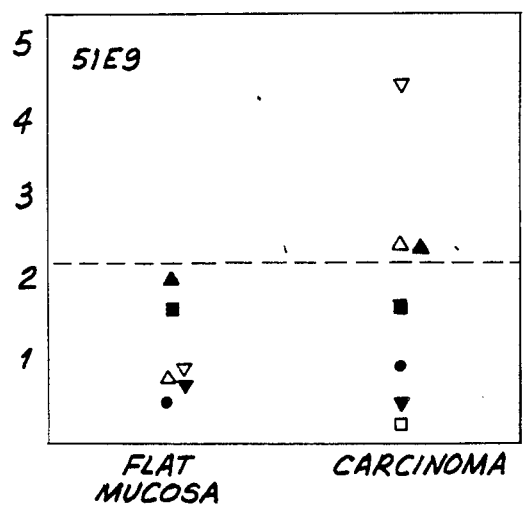
Figure 5D:
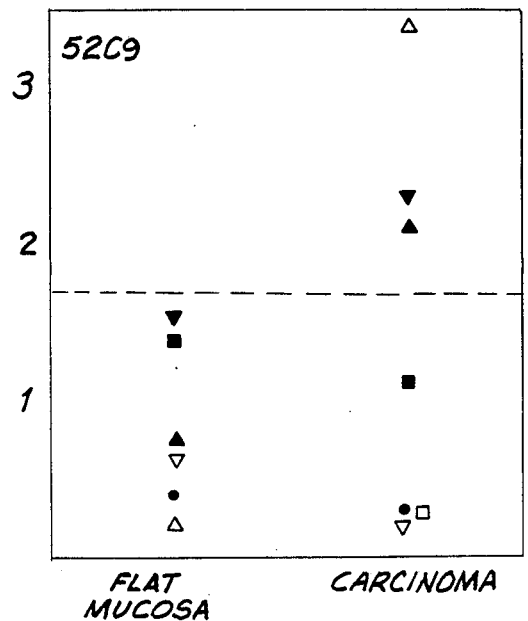
Figure 5E:
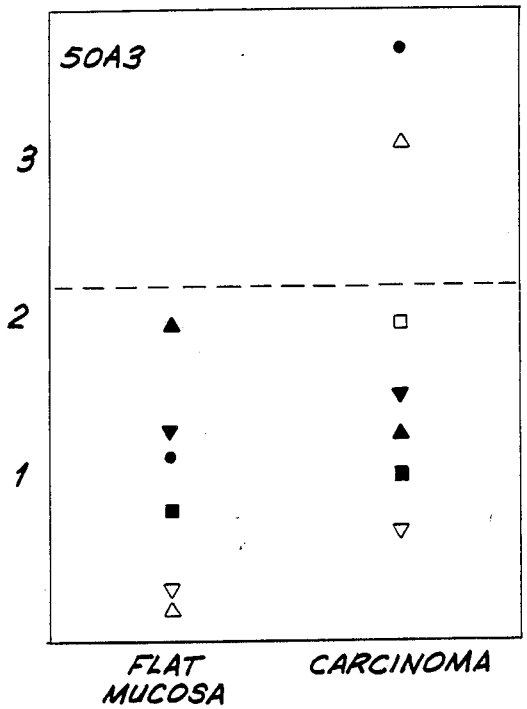

The comparisons of each of these tissues (low-risk flat mucosa, adenoma and carcinoma) to the high-risk ACR flat mucosa is very different (FIGS. 2d, e, f). The distribution is skewed in each case, with a large number of sequences showing substantial increases (3 to 10 fold) and decreases (60 to 80%). This same conclusion can be reached from the data of FIG. 3. Here is plotted the distribution of sequences which differ in level of expression at several significance levels (Student's t test) for each of the comparisons. While comparisons of low risk flat mucosa, adenoma, and carcinoma reveal some sequences which are altered in expression at various significance levels, the number of such sequences is much less than the difference between each of these tissue types and the high risk flat mucosa. Therefore, from the data presented in FIGS. 2 and 3, the disclosed technique can distinguish high risk (ACR) flat mucosa from low risk, and also from adenoma (benign tumor) and carcinoma.

The distinctions between low risk flat mucosa, adenoma, and carcinoma become more clear when the data are analyzed in a different way. FIGS. 4a-d present the individual data points for four of the 379 clones (i.e, clone 50D5, 51A12, 51E2, and 52B10) for each of the adenoma and each of the carcinoma biopsies. For each clone, a line has been drawn at a level of expression which distinguishes all or most of the carcinomas from the adenomas. In tabulating the results of these data (Table I) it can be seen that all of the carcinomas can be distinguished from adenoma on the basis of expression of these four sequences, using the cut-offs indicated in FIG. 4. For carcinomas 2, 11, and 28 (Table I), this involves differences in expression of two of the four clones (51A12) and 52B10). For carcinomas 1 and 12, expression of three of the clones is altered, while for carcinomas 23 and 26, all four clones are altered in expression. Table I also illustrates that using the cut-offs indicated in FIG. 4, several of the adenomas express sequences in a manner characteristic of carcinoma. In each case, however, this involves an altered expression of just one of the four clones. Hence, by comparing the patterns of expression of a number of sequences in the carcinomas and adenomas, all of the malignant tumors can be distinguished from all of the adenomas.

TABLE I

| Carcinoma | 50D5 | 51A12 | 51E2 | 52B10 |
|---|---|---|---|---|
| 1 | X | X | | X |
| 2 | | X | | X |
| 11 | | X | | X |
| 12 | X | | X | X |
| 23 | X | X | X | X |
| 26 | X | X | X | X |
| 28 | | X | | X |
| Adenoma | | | | |
| 3 | | X | | |
| 4 | | X | | |
| 10 | | | | |
| 15 | | | | |
| 16 | | | | |
| 19 | | | | X |

X = distinguished from adenoma

A similar analysis was done in comparing the malignant tissue to the low risk flat colonic mucosa. Here, five clones are selected (50D5, 51E9, 52A12, 52C9, and 50A3). The data for each of the carcinoma and each of the flat mucosa biopsies for each clone, and the selected cut-off levels, are presented in FIGS. 5a–e and summarized in Table II.

TABLE II

| Carcinoma | 50D5 | 51E9 | 52A12 | 52C9 | 50A3 |
|---|---|---|---|---|---|
| 1 | X | | | | X |
| 2 | | | | | |
| 11 | | X | | X | X |
| 12 | X | | X | | |
| 23 | X | X | X | | |
| 26 | X | X | X | X | |
| 28 | | | | X | |
| low-risk flat mucosa | | | | | |
| 5 | | | | | |
| 14 | | | | | |
| 17 | | | | | |
| 20 | | | | | |
| 24 | | | | | |
| 27 | | | | | |

X = distinguished from low-risk flat mucosa

On the basis of expression of these five clones, 6 of 7 of the malignant tissues can be distinguished from all of the normal tissue. One biospy sample (number 2) classified as carcinoma would not be distinguished from the normal tissue as regards expression of these five sequences. Retrospective examination of the pathology reports revealed that although this biopsy was originally removed as carcinoma, it was subsequently evaluated as an area of inflammation in a patient who has previously had colon carcinoma. Our data can therefore distinguish between frank carcinoma and tissue which grossly appears to be transformed but which most likely is not.

It is important to note that for these two analyses (Tables I and II), the distinction between all members of each set could not be made on the basis of expression of only one sequence. The demonstration of a pattern of expression of a number of sequences, however, could be used to characterize the tissue type, and in most cases this could be confirmed by a pattern of expression of more than one sequence. This is the value of the concept of the quantitation of level of expression of each of large numbers of cloned sequences which is described. It is important to note that the concept is independent of the determination of which sequences are functionally more significant in dictating the cell or tissue phenotype or whether every sequence which is important in determination of the phenotype that is identified. Instead, advantage is taken of the large number of differences in gene expression which exist between different cell and tissue types. The data presented illustrate the usefullness of this approach in making clinically important determinations, for example distinguishing between low and high risk tissue, and between stages in progression of disease from normal, to benign tumors to malignant tumors.

The patterns that have been recognized which permit the characterization of each of the phenotypes described are readily detected. As the number of subjects is increased and finer classifications are attempted (e.g., among the flat mucosa in populations which show more subtle differences in risk for colon cancer, or between carcinomas which metastasize to different sites or respond differently to various drug regimens) those skilled in the art may select larger numbers of cloned sequences in order to recognize complex patterns of expression. These selections may be made using the same approach that is disclosed hereinabove without the exercise of inventive faculity. The procedures disclosed hereinabove accomplish the task of quantitating the relative level of expression of each of many thousands of cloned sequences in order to provide data sufficient to characterize cell or tissue phenotype. It is the development of this large data base of information which provides the means for diagnosis and prognosis of disease, and evaluation of risk. The data may, however, be generated in several different ways, each having advantages and disadvantages over the methodology described. The invention may be practiced using the alternatives to the disclosed methodology that are described below.

To synthesize probes which represent a mRNA population for hybridization, several alternatives to reverse transcription using 32P labeled deoxynucleotides for synthesis of probes can be used.

a. the RNA can be cleaved by nuclease to smaller fragments and each fragment end-labeled by addition of a 32P molecule using polynucleotide kinase and gamma 32PATP, as described by Derman et al., Cell 23 p. 731 (1981). Such labeled molecules can be used to hybridize to nucleic acid bound to nitrocellulose or other matrices. They avoid potential errors in representation of sequences in a population of such probes, but often give much higher backgrounds and hence are not as suitable for scanning and quantitation.

b. In order to improve the representativeness of the probe, the RNA can be reverse transcribed using either avian or murine reverse transcriptase and random primers which, are short oligodeoxynucleotide sequences of sufficient complexity that provide fragments which will hybridize randomly over every RNA molecule in the reaction and provide multiple sites of initiation for the reverse transcriptase along each polynucleotide.

c. 35S labeled deoxynucleotides can be used in place of the 32P labeled deoxynucleotides in order to label the probe for subsequent detection. The use of 35S deoxynucleotides is suitable for reverse transcription using either oligo dT primers or random primers and using avian or murine reverse transcriptase. 35S decays less rapidly than 32P, and hence permits longer exposure times and simplifies multiple exposures. In addition, the emission resulting from 35S decay has less energy, and the signal therefore yields a smaller spot on the x-ray film. This results in several potential improvements, including the ability to assay a larger number of sequences in a smaller area with less chance of overlap of signal during scanning and data digitization.

d. Reverse transcription with avian or murine reverse transcriptase, and with oligo dT or random primers can also be done with 125 I labeled deoxycytidine. Such probes, due to the high specific activity of 125I and high energy of emission, would require shorter exposure times than probes synthesized using 32P or 35S.

e. A variety of methods for probe preparation which do not depend on subsequent detection of radio-activity are available and appropriate. Biotinated probes can be synthesized using biotin conjugated dUTP. This can be done with either avian or murine reverse transcriptase, and oligo dT or random primers. Detection, of such probes is done using an indirect immunoassay, with signal generated by either flourescent, substrate, or enzyme linked antibodies.

f. Labeling the probe with biotin or 125 I can be done chemically rather than enzymatically. These chemical reactions are described in Prensky W. et al, Proc. Nat. Acad. Sci. U.S.A. 70 1860 (1973); Broker TR, Nuc. Acids Res. 5, 363 (1978); and Sodja and Davidson Nuc. Acids Res. 5, 385 (1978), which are incorporated by reference. They provide the advantage of eliminating possible bias of the enzyme (reverse transcriptase) and therefore may produce a more representative probe.

Several new matrices which are suitable alternatives to nitrocellulose for growth of the clones and/or fixing nucleic acid for subsequent hybridization (below) are available. These include NYTRAN from Schliecher and Schuell and GENESCREEN from New England Nuclear Corp. In general, any matrix upon which the clones can be grown or nucleic acid fixed in a patterned array is suitable.

The method described herein employs sequences cloned in plasmid vectors propagated in bacteria. It is also possible to use bacteriophage vectors. In this case, each plaque would be picked and arrayed in a microtiter plate. To replica plate the cloned sequences in the microtiter plate, the replicating device may be charged by insertion into the microtiter plate and then gently impressed on an agar plate which had a layer of top agar freshly poured and inoculated with the host bacterial strain. Following overnight growth, an amalgam of many bacteriophage plaques will appear at the position of each of the prongs of the replicating device. Standard plaque lifts by the method of Benton and Davis (1977) transfer these phage to nitrocellulose or other medium. They can then be prepared for hybridization by standard methodology Benton and Davis (1977).

4. Use of purified nucleic acid.

Replica plating of the bacteria in patterned arrays, followed by growth, lysis, and fixation of the nucleic acid to the filter for subsequent hybridization is the most convenient way to assay each of large numbers of sequences. Using purified nucleic acid for the generation of the patterned arrays is also suitable and in some ways desirable. To do this, palsma or bacteriophage preparations would be made from each of the selected clones, the DNA denatured, and deposited in uniform spots in a patterned array, individually spotting the DNA, or by using any one of several available devices made for this purpose. The use of purified DNA will produce more uniform spots, each of whose intensity can in turn be read by a microtiter plate reader, which are available from several sources (e.g., Bio-Tek). The uniformity of the spot density and positioning also permits use of any type of x-ray film scanner for recording of the results. In the case of hybridization with biotin and subsequent detection by fluorescence or enzymatic color development, those skilled in the art may select an appropriate scanner.

The invention also includes an automated procedure which comprises producing the dot blots in a rigid array so that the position of each sequence is precisely defined. This can be done using any one of several available devices which produce dot blots in a 96 position (8×12) pattern. Using these apparatus can then be constructed consisting of a pattern of blades or hole-punch units which divides the resultant blot into 96 sections, each section corresponding to the location of one sequence. The sections are then inserted into a scintillation vial, which is then cooled in a scintillation counter. Data from the scintillation counter is either manually entered into a data base, or entered by direct link between the scintillation counter and a computer.

Figure 6:
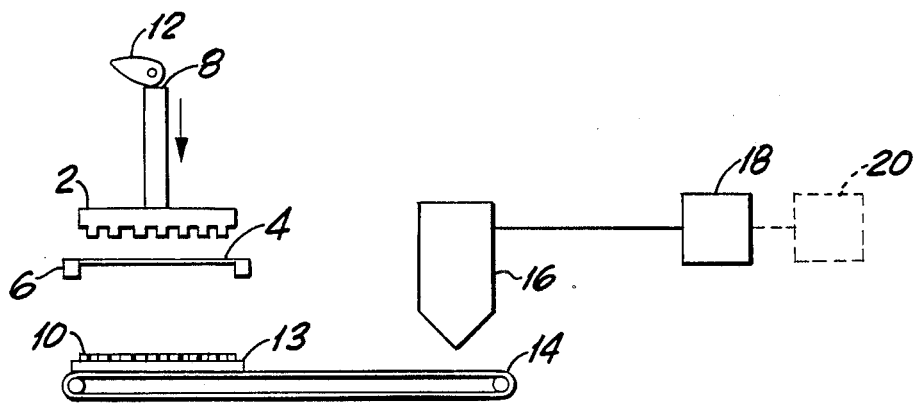
FIG. 6. is a schematic of an apparatus of the invention.

The apparatus of the invention may comprise sectioning means for isolating each of the clones from the filter; conveying means for moving the isolated clones to a detector; detecting means for analyzing each clone; and recording means for making a record of the results of each analysis. FIG. 6 is a schematic of an apparatus according to the invention which shows a multiple headed punch 2 positioned above a filter 4 which is supported by bracket 6. Force is applied to the multiple headed punch 2, which is held in register with the filter by a positioning template (not shown), to cut out the individual clones 10. The force is applied to piston 8 by an electrically operated cam 12 or by a manually activated lever. The individual clones 10 are deposited on holder 13 in the same order in which they are cut. If a rectangular pattern of clones is used, they may be sectioned into linear strips before being placed in the multiple headed punch. It is also contemplated that a punch may be used to punch out rectangular patterns of clones that are sorted before being placed on the holder so that they are spaced far enough apart to avoid interference when they are passed by the scintillation counter. If the fluorescent technique is used then fluorescent detecting means are utilized.

A conveyor 14 may be used to move the holder 13 past the scintillation counter 16. The counts are recorded by a digital analyzer 18 which may be connected to a printer 20.

These publications are cited hereinabove and they are incorporated by reference:
1. Hastie, N. D. and Bisphop, J. O., Cell 9, 761 (1976);
2. Slamon, D. J., de Kernion, J. B., Verma, I. M., and Cline, M. J., Science 224, 256 (1984);
3. Groudine, M. and Weintraub, H., Proc. Nat'l. Acad. Sci., USA 77, 5351 (1980);
4. Grunstein, M. and Hogness, D., Proc. Nat'l. Acad. Sci., USA 72, 3961 (1975);
5. Benton, W. D. and Davis, R. W., Science 196, 180 (1977);
6. Dworkin, M. B. and Dawid, I. B., Dev. Biol. 76, (1980);
7. Zimmerman, C. R., Orr, W. C., Le Clerc, R. F., Barnard, E. C., and Timberlake, W. E., Cell 21, 709 (1980);
8. Williams J. G. and Lloyd, MM., J. Mol. Biol. 129, 19 (1979);
9. Lasky, L. A., Lev, Z., Xin, J. H., Britten, R. J., and Davidson, E. H., Proc. Nat'l. Acad. Sci., USA 77, 5317 (1980);
10 St. John, T. P. and Davis, R. W., Cell 16, 443 (1979);
11. Crampton, J., Humphries, S., Woods, D., and Williamson, R., Nuc. Acids Res. 8, 6007 (1980);
12 Augenlicht, L. H. and Kobrin, D., Cancer Res. 42, 1088 (1982);
13. Gergen, J. P., Stern, R. H., and Wensink, P. C., Nuc. Acids Res. 7, 2115 (1979);
14. Maniatis, T., Fritsch, E. F., and Sambrook, J. (1982), Molecular Cloning, A Laboratory Manual, Cold Spring Harbor Laboratory, N.Y.;
15 Aviv, H. and Leder, P., Proc. Nat'l. Acad. Sci., USA 69, 1408 (1972); and
16 Dagert, M. and Ehrlich, S. D., Gene 6, 23 (1979).

I claim:

1. A method for the determination of the presence of a malignant or premalignant condition in human tissue or for the determination of risk for development of a malignant or premalignant condition in human tissue, said method comprising the steps of:

(a) isolating RNA from tissue that is to be determined;
(b) preparing a probe using RNA from step (a);
(c) hybridizing to the probe of step (b) a plurality of cloned gene sequences which are unrestricted as to function to form a plurality of hybridized probes;
(d) exposing the hybridized probe to detecting means to quantify the extent of hybridization; and
(e) comparing the extent of the hybridization obtained in step (d) with a known standard to determine the existence of malignant or premalignant tissue or the presence of risk for development of malignant or premalignant condition in human tissue.

2. A method for the determination of the presence of a malignant or premalignant conditions in human tissue as defined in claim 1 wherein the hybridized probe of step (c) is prepared with a material which generates a signal, said material being selected from the group consisting of radioactive probes, immunoreactive probes, or fluorescent probes, phosphoresent probes, luminescent probes or enzymatic probes.

3. A method for the determination of the presence of malignant or premalignant conditions in human tissue as defined in claim 2 wherein the hybridized probe is labeled with a radioactive probe.

4. A method for the determination of the presence of malignant or premalignant conditions in human tissue as defined in claim 3 wherein the detecting means comprise a radioactive probe X-ray films.

5. A method for the determination of the presence of malignant or premalignant conditions in human tissue as defined in claim 4 wherein the film is read by an optical scanner that feeds a signal to a computer that converts the signal to digital form.

6. A method for the determination of the presence of malignant or premalignant conditions as defined in claim 5 wherein the known standard comprises a library of digitized data obtained from a plurality of cloned sequences.

7. A method for the determination of the presence of malignant or premalignant conditions as defined in claim 6 wherein the known standard comprises a plurality of clones derived from RNA from malignant tissue.

8. A method for the determination of the presence of malignant or premalignant condition in human tissue as defined in claim 7 wherein the cloned gene sequences are maintained in a culture of *E. coli*.

9. A method for the determination of the presence of a malignant or premalignant condition or for the determination of the risk for the development of a malignant or a premalignant condition in human colonic mucosa, said method comprising the steps of:

(a) isolating RNA from human colonic tissue that is to be determined;
(b) preparing a probe using RNA from step (a);
(c) hybridizing the probe from said human colonic tissue to a plurality of cloned gene sequences in a strain of *E. coli* on filter media, said cloned gene sequences being derived from malignant or premalignant human colon tissue to form a plurality of hybridized probes;
(d) labeling said plurality of hybridized probes with a radioactive tracer;
(e) detecting the degree of hybridization by radiation detecting means that measure the intensity of the tracer on said hybridized probes;
(f) converting the measured intensity of the said tracer to digital data; and
(g) comparing the digital data obtained in step (f) with a known standard to determine the existence of said malignant or premalignant tissue.

10. A method for the determination of the presence of a malignant or premalignant condition in human colonic mucosa as defined in claim 9 wherein the degree of hybridization in step (d) is carried out using X-ray film.

11. A method for the determination of the presence of a malignant or premalignant condition in human colonic mucosa as defined in claim 10 wherein an optical scanner is used to convert images on said X-ray film to digital data.

12. A method for the determination of the presence of a malignant or premalignant condition in human colonic mucosa as defined in claim 11 wherein the digital data is compared with a known standard using computer means.

13. A method for the determination of the presence of a premalignant condition in human tissue or for the determination of risk for development of a premalignant condition in human tissue, said method comprising the steps of:

(a) isolating RNA from tissue that is to be determined;
(b) preparing a probe using RNA from step (a);
(c) hybridizing to the probe of step (b) a plurality of cloned gene sequences, which are unrestricted as to function, from a human colon carcinoma cell line to form a plurality of hybridized probes;
(d) exposing the hybridized probe to detecting means to quantify the extend of hybridization; and
(e) comparing the extent of the hybridization obtained in step (d) with a known standard to determine the existence of premalignant tissue or the presence of risk for development of a premalignant condition in human tissue.

* * * * *